US00PP16587P2

(12) United States Plant Patent
Avent et al.

(10) Patent No.: US PP16,587 P2
(45) Date of Patent: May 30, 2006

(54) ***ECHINACEA* PLANT NAMED 'PARANOIA'**

(50) Latin Name: *Echinacea purpurea×paradoxa*
Varietal Denomination: Paranoia

(76) Inventors: Tony Avent, 9241 Sauls Rd., Raleigh, NC (US) 27603; Richard Saul, 308 Hester Valley Rd., Cleveland, GA (US) 30528

( * ) Notice: Subject to any disclaimer, the term of this patent is extended or adjusted under 35 U.S.C. 154(b) by 100 days.

(21) Appl. No.: 10/902,991

(22) Filed: Jul. 30, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—June Hwu

(57) ABSTRACT

A new and distinct cultivar of *Echinacea* plant named 'Paranoia', characterized by its short, compact plant habit and buttery yellow reflexed ray flowers arranged around a coppery-brown cone of many disc florets.

2 Drawing Sheets

Genus: *Echinacea.*
Species: *purpurea×paradoxa.*
Denomination: 'Paranoia'.

BACKGROUND OF THE INVENTION

The present Invention relates to a new and distinct cultivar of coneflower that may be grown for use as an ornamental plant in containers and in the garden or landscape. The new cultivar is known botanically as *Echinacea purpurea* times *paradoxa* and will be referred to hereinafter by the cultivar name 'Paranoia'.

'Paranoia' arose and was selected in 1999 as a single plant grown from approximately 100 seeds which the Inventors had obtained in the fall of 1997 from the deliberate pollination carried out in Dahlonega, Ga. in the summer of 1997 of the cultivar of *Echinacea purpurea* known as 'White Swan' (unpatented) by pollen collected from plants of the species *Echinacea paradoxa* (species, unpatented).

*Echinacea purpurea* is widely grown in commerce and known as the purple coneflower. Most cultivars of *Echinacea* are selections of *Echinacea purpurea* which exhibit pink to purple flowers; *Echinacea purpurea* 'White Swan' exhibits white flowers with light copper tones.

*Echinacea paradoxa* is known and grown only as the species, with plants being raised from seed saved from plantings of the species. No cultivars of *Echinacea paradoxa* are known to the Inventors. *Echinacea paradoxa* is uniquely yellow flowered and occurs naturally in the prairies of Missouri and Arkansas and in the Ozark mountains. *Echinacea paradoxa* is, however, poorly suited to commerce, being tall (up to 3 feet) and lax in habit.

The approximately 100 seeds obtained from the cross described above were sown by the Inventors in Raleigh, N.C. in the fall of 1997. Only two seeds were found to germinate and the resulting seedlings were observed for a further two years. In 1999, one of the two plants was selected for its satisfactory vigor and ability to produce attractively branched plant habit. This one plant, which is the subject of the instant application, was isolated for asexual propagation; the other plant was discarded.

Asexual reproduction of the new *Echinacea* plant 'Paranoia' was first conducted by the Inventors in a cultivated area known as Plant Delights Nursery, Raleigh, N.C. The method used was division of the whole plant, including the roots. The plants thus obtained were observed to exhibit identical characteristics to the plant of 'Paranoia' originally selected. The claimed variety 'Paranoia' has been determined true to type after successive cycles of asexual reproduction, originally by division as above and subsequently by means of tissue culture.

SUMMARY OF THE INVENTION

The cultivar 'Paranoia' has not been observed under all possible environmental conditions. The phenotype may vary somewhat with variations in environment such as temperature and light intensity without, however, any variance in genotype.

The following traits have been repeatedly observed and are determined to be the unique characteristics of 'Paranoia'. These characteristics in combination distinguish 'Paranoia' as a new and distinct *Echinacea:*

1. Short, compact plant habit, typically 40 cm–45 cm high after one growing season
2. Buttery yellow reflexed ray flowers
3. Coppery-brown cone composed of many disc florets
4. Apparent sterility: no seed has been observed.

When compared with the male parent, the species *Echinacea paradoxa,* 'Paranoia' exhibits similar flower color but greatly reduced height combined with branching habit and flower stems arising from each basal branch.

When compared with the female parent, the cultivar *Echinacea purpurea* 'White Swan', 'Paranoia' exhibits yellow flowers which, to the Inventors, are unknown within cultivars of this species. Moreover, *Echinacea purpurea,* 'White Swan' achieves far greater height, approaching 36 inches in one growing season.

When compared with other described cultivars of *Echinacea purpurea* or of *Echinacea purpurea* times *paradoxa,* 'Paranoia' appears to be novel by combining short flowering height with yellow coloration of flower. Other cultivars which are listed at similar heights of 18–24 inches, carry purple flowers which are typical of the species *E. purpurea.* The color yellow is not found in *E. purpurea* but has been described in varieties of the inter-specific hybrid *E. purpurea* times *paradoxa.* However such cultivars appear generally to retain the typical height of *E. purpurea,* namely 30 inches or taller.

BRIEF DESCRIPTION OF THE DRAWINGS

The accompanying color drawings illustrate the overall appearance of the new *Echinacea* cultivar 'Paranoia' showing the colors as true as it is reasonably possible to obtain in colored reproductions of this type. Colors in the photographs may differ from the color values cited in the detailed botanical description, which accurately describe the actual colors of the new variety of 'Paranoia'.

Figure 1:
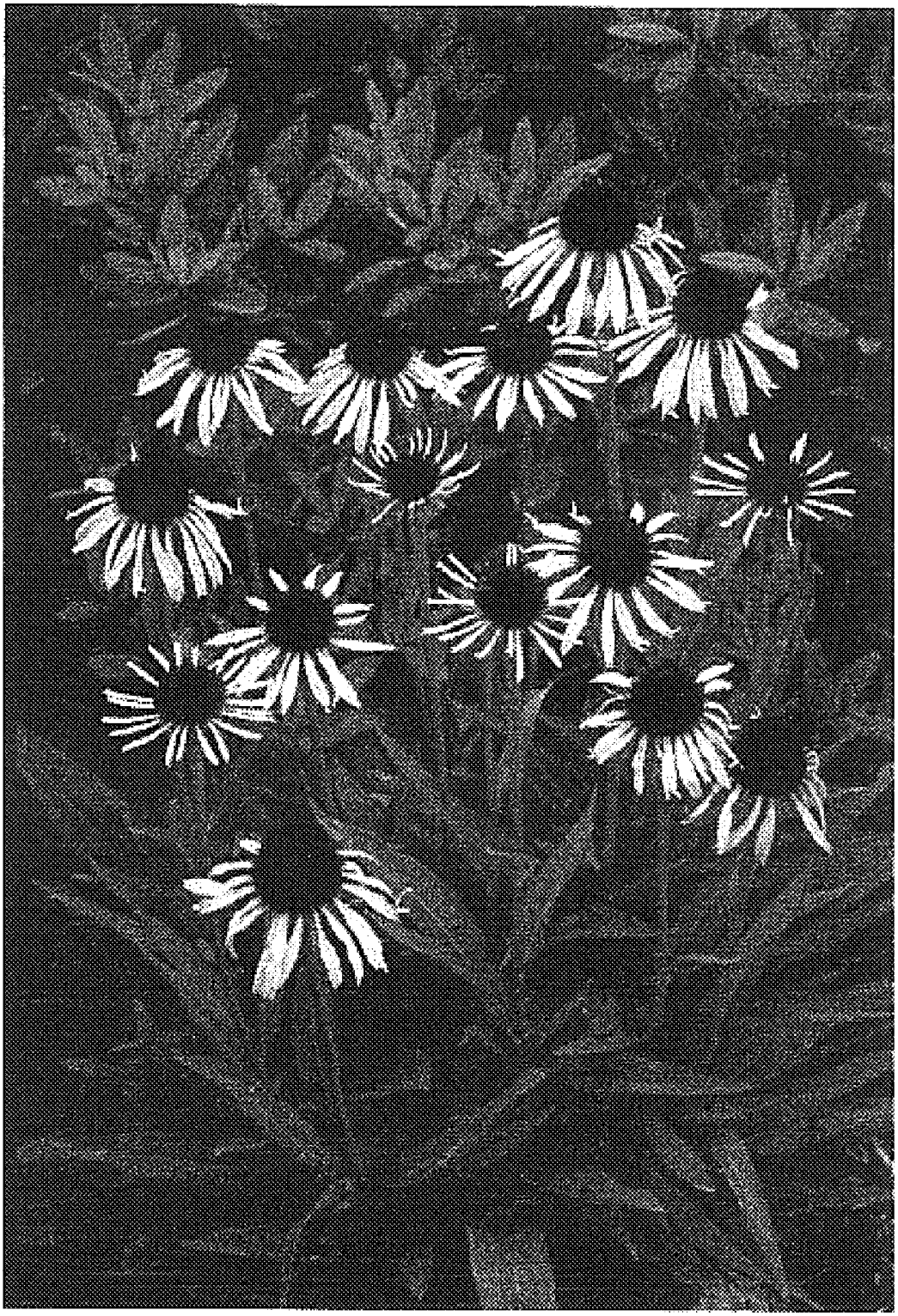
FIG. 1 illustrates an entire plant of 'Paranoia' in bloom, from a side perspective. This plant is approximately two years old and is planted in open ground in Raleigh, N.C.
Figure 2:
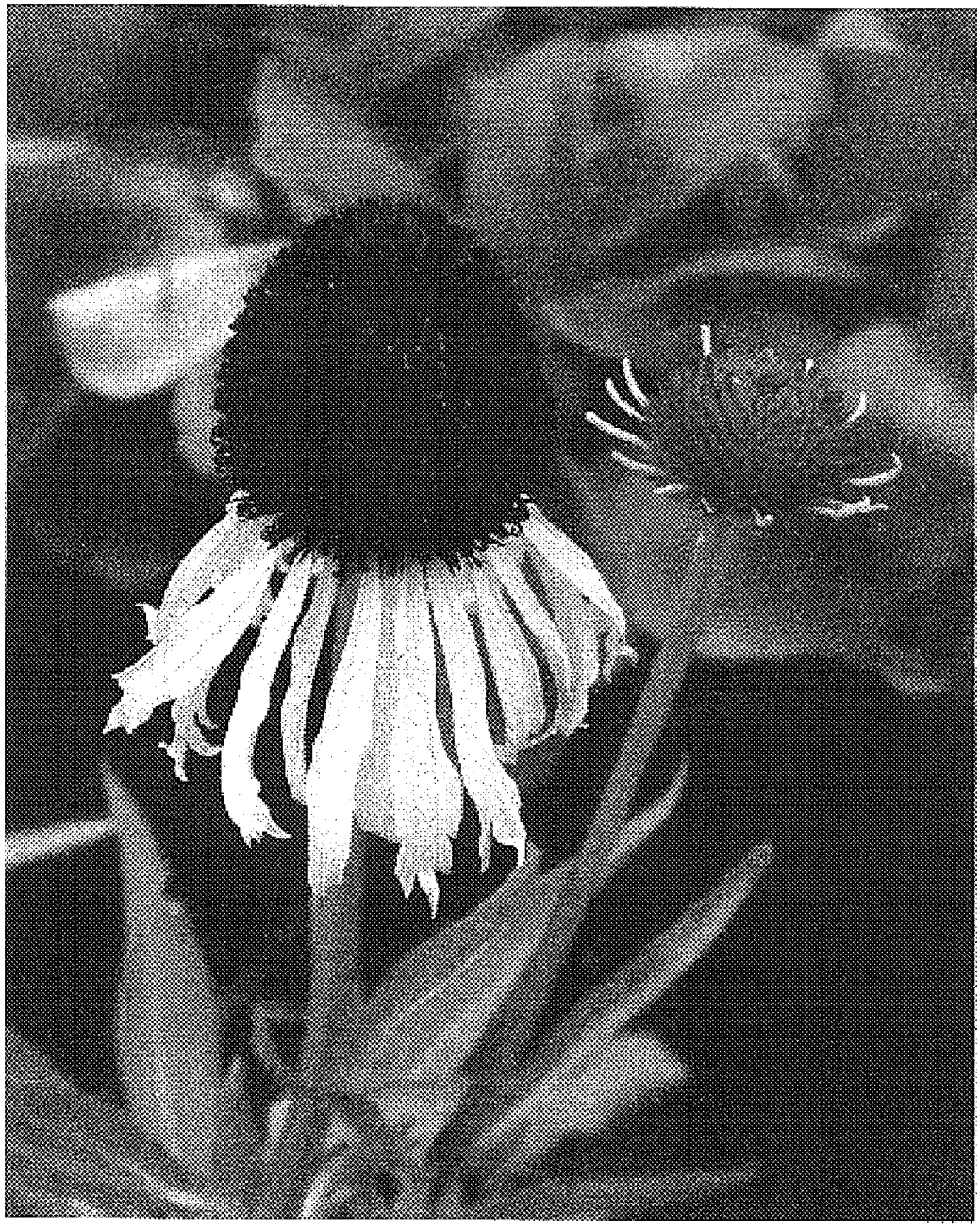
FIG. 2 illustrates a close-up view of the inflorescence showing both ray florets and the disc florets which constitute the typical spiny cone of *Echinacea.*

The drawings are made using conventional photographic techniques and although flower and foliage colors in the photographs may differ from the actual colors due to light reflectance, they are as accurate as conventional photography can portray.

BOTANICAL DESCRIPTION OF THE PLANT

The aforementioned photograph and following observations and measurements describe plants of 'Paranoia' grown outdoors in Raleigh, N.C. in full sun.

The observed plants were approximately two years old from a single division.

Color observations were made by reference to the 2001 edition of The Royal Horticultural Society Colour Chart, except where general terms of ordinary dictionary significance are used.

Botancial classification:
- *Genus.*—*Echinacea.*
- *Species.*—*Purpurea* times *paradoxa.*
- *Cultivar denomination.*—'Paranoia'.
- *Parentage.*—Induced hybrid between the species *Echinacea paradoxa* (male parent) and the cultivar *Echinacea purpurea* 'White Swan' (female parent).

Propagation:
- *Method.*—Crown division and tissue culture.
- *Time to produce a rooted plant.*—Division (with roots attached) 10 days to re-establish. Tissue Culture explant: 4–6 weeks.

Root description: Deep, fine, fibrous, well-branched.

Overall plant description:
- *Appearance.*—Herbaceous perennial with upright habit and short stature and basal branching habit with lateral flowering branches.
- *Vigor.*—Not vigorous.
- *Height, including flowers, after one growing season.*—Approximately 40 cm–45 cm.
- *Width after one growing season.*—Approximately 50 cm–55 cm.

Growing conditions:
- *Soil types.*—Preference for deep loam or sandy loam.
- *Hardiness.*—Survives in Zone 4B.
- *Heat tolerance.*—Tolerates extreme heat and humidity of the south-eastern United States.

Pest and disease resistance and susceptibility: None of note in comparison with the genus *Echinacea* which can be susceptible to chewing insects and to pathogens including *fusarium, sclerotinia, phytopthera, verticillium.*

Basal branches:
- *Length.*—About 20 cm–25 cm.
- *Diameter.*—About 4 mm–6 mm.
- *Internode length.*—About 5 cm.
- *Aspect.*—Upright.
- *Strength.*—Stiff.
- *Texture.*—Pubescent: stiff short bristly hairs approximately 1 mm–2 mm in length, color grayish-white.

Foliage description:
- *Arrangement.*—Alternate, single.
- *Attachment.*—Petiolate towards the base, becoming sessile towards tip.
- *Length.*—Ranges from 13 cm to 30 cm.
- *Width.*—Ranges from 20 mm to 35 mm.
- *Shape.*—Lanceolate.
- *Apex.*—Acuminate.
- *Base.*—Cuneate.
- *Margin.*—Entire.
- *Texture, upper and lower surfaces.*—Slightly pubescent.
- *Color.*—Dark green, 146A (both surfaces).
- *Venation pattern.*—Parallel.
- *Venation color.*—Yellow-green, approximately 146D (both surfaces).

Petiole:
- *Dimensions.*—Length (basal leaves) Approximately 9 cm. Diameter: Approximately 2 mm.
- *Texture.*—Upper and lower surfaces: Smooth.
- *Color, upper and lower surfaces.*—146D.

Inflorescence:
- *Appearance.*—Solitary flowers held above the foliage canopy on stiff upright peduncles. Consists of yellow narrow drooping toothed ray flowers (petal-like) arranged radially around coppery-brown conical disk florets.
- *Flowering period.*—In the South-East of the US: continuously from late May until late June, and sporadically until September.
- *Number of individual flowers* (*flower heads*).—One per stem; from five to twenty flowering stems (buds and open flowers) at any one time during the growing season.
- *Lastingness of an individual flower.*—Approximately 10–15 days from first emergence of ray flowers until their senescence.
- *Fragrance.*—None noticed.
- *Bud* (*consists of involucral cone and first emerging ray petals*).—Shape: Flattened ellipse. Dimensions: Diameter of cone approximately 2 cm to 2.5 cm. Depth (height) of bud: approximately 0.5 cm. Color: involucres yellow-green approximately 144A with tan colored pales approximately N170A.
- *Inflorescence* (*ray florets fully developed*).—Shape: Rounded cone with ray florets drooping. Dimensions (cone only): Diameter: Ranges from 4 cm–6 cm. Height: Slightly exceed diameter, from 4 cm–7 cm. Dimensions (entire inflorescence, cone and ray florets expanded and drooping at 20 degrees below the horizontal): Diameter: Ranges from 8 cm–12 cm. Height: Ranges from 5 cm–8 cm. Dimensions (entire inflorescence, cone and ray florets expanded and drooping at 75 degrees below the horizontal, prior to senescence). Diameter: Ranges from 6 cm–8 cm. Height: Ranges from 7 cm–to 10 cm.

Ray florets (pseudo-petals):

*Dimensions.*—Length: Approximately 4 cm. Width: Approximately 5 mm.

*Shape.*—Strap-like ligules.

*Apex.*—Irregularly toothed.

*Teeth.*—Typically 2 or 3 in number, 2 mm–4 mm in length; 0.5 mm–1.5 mm in width.

*Base.*—Acute.

*Margin.*—Entire.

*Texture.*—Smooth (both upper and lower surfaces).

*Aspect.*—At first emergence, typically 10 degrees above the horizontal. When fully expanded: 20 degrees below the horizontal. When fully developed and aged: 75 degrees below the horizontal.

*Number per inflorescence.*—Ranges from 15 to 22.

*Color.*—Buttery yellow, approximately 10A (all stages, both surfaces).

Disc florets:

*Shape.*—Corolla cylindrical, tubular with five lobes, surrounded by phyllaries which transform into scaly pales which protrude beyond apex of corolla.

*Apex* (*corolla*).—Obtuse.

*Apex* (*pales*).—Sharply acute.

*Dimensions* (*including pales*).—Length: Approximately 5 mm. Width: Approximately 2 mm.

*Number of disc florets per infloresence.*—Approximately 300.

*Color.*—Initially yellow-green corolla approximately 144A with tan colored pales approximately N170A. Florets fully developed, corolla obscured or inconspicuous, pales copper-brown, ranges between N34A and 183A.

Phyllaries:

*Arrangement.*—Imbricate, in series of two or more.

*Dimensions.*—Approximately 3 mm in length and 1 mm in width.

*Shape.*—Elliptic.

*Apex.*—Acute.

*Base.*—Fused.

*Margin.*—Entire.

*Number per inflorescence.*—Approximately 300.

*Color.*—144A (visible outer surface) Pales: Dimensions: Length: Approximately 5 mm (extending 1 mm beyond apex of corolla). Width: Approximately 1 mm at apex of corolla, then sharply tapering to acute pale apex. Shape: Longitudinally folded, sheath-like. Surface: Smooth.

*Peduncles.*—Dimensions: Length: Approximately 15 cm–20 cm. Diameter: Approximately 4 cm.

*Angle.*—Erect.

*Strength.*—Stiff, strong.

*Texture.*—Highly pubescent with very short soft fine gray hairs.

*Color.*—143C.

Reproductive organs:

*Androecium* (*ray florets*).—Absent.

*Androecium* (*disc florets*).—Present. Stamens: Number: 5, filaments distinct, basifixed. Shape: linear, longitudinally folded to base of apex. Apex: Hastate. Dimensions: 6 mm in length (from base of corolla); 0.5 mm in width. Color: Light brown: lighter than 200D, except margins appear darker, closest to 200D. Anther: Shape: oblong. Dimensions: 4 mm in length; 0.25 mm in width. Color: Dark brown with reddish tint, close to 178A. Pollen: Copious, arising from longitudinally dehiscing anthers. Color and texture: Translucent yellow, globose. Particle size: Tiny.

*Gynoecium* (*ray florets*).—Absent.

*Gynoecium* (*disc florets*).—Present. Pistils: 1, with two carpels. Pistil length (including ovary, style, stigma) approximately 1 cm. Stigma: Shape: Coiled, split with two styles. Stigma: Color: (abaxial surface): Light green. Stigma: Color (adaxial surface): Bronze red with translucent reddish hairs. Style: Length approximately 5 mm, light green in color, with slight shading of bronze-red at connection to stigma and style.

Seed: None has been observed.

It is claimed:

1. A new and distinct variety of *Echinacea* plant named 'Paranoia' as described and illustrated herein.

* * * * *